Figure 1:
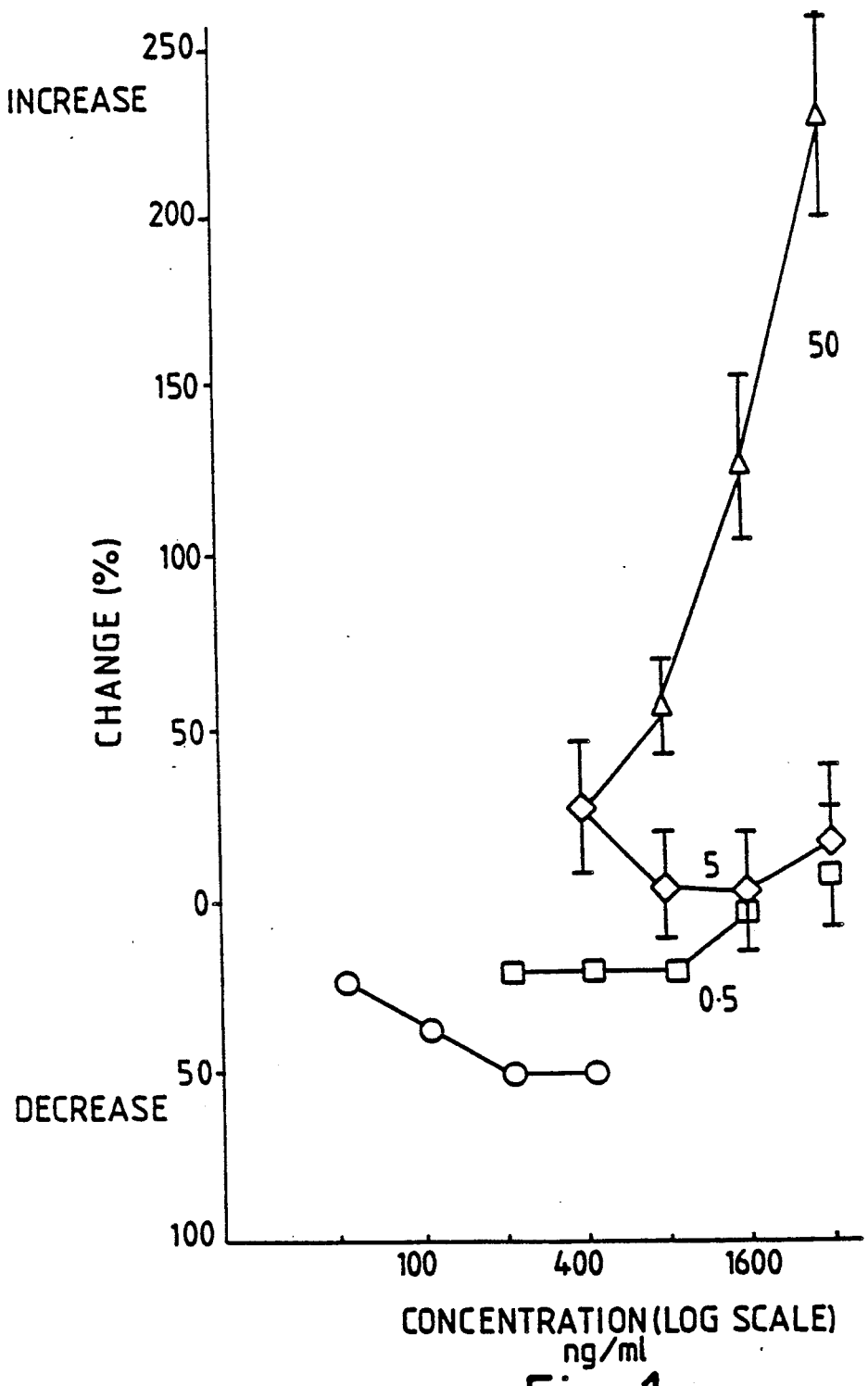

United States Patent [19]

Rees et al.

[11] Patent Number: 4,996,223

[45] Date of Patent: Feb. 26, 1991

[54] NEW ORGANIC COMPOUNDS HAVING OPIOID PROPERTIES

[75] Inventors: John M. H. Rees, Knutsford; Brian Robinson, Glossop, both of United Kingdom; Brian Cox, Montclair, N.J.

[73] Assignee: The Victoria University of Manchester, Manchester, United Kingdom

[21] Appl. No.: 295,037

[22] PCT Filed: Jun. 30, 1987

[86] PCT No.: PCT/GB87/00457
§ 371 Date: Feb. 9, 1989
§ 102(e) Date: Feb. 9, 1989

[87] PCT Pub. No.: WO88/00193
PCT Pub. Date: Jan. 14, 1988

[30] Foreign Application Priority Data

Jul. 2, 1986 [GB] United Kingdom ............... 8616089

[51] Int. Cl.$^5$ .................... C07D 487/06; A61K 31/40
[52] U.S. Cl. ..................................... 514/410; 548/421
[58] Field of Search ............... 548/421, 429; 514/411, 514/410

[56] References Cited

FOREIGN PATENT DOCUMENTS 1205105 11/1965 Fed. Rep. of Germany.
2005259 4/1979 United Kingdom.

OTHER PUBLICATIONS

Liebigs Annalen der Chemie, vol. 709, 1967, Fritz et al.: "Über Ring-Ketten-Tautomerie ... ", pp. 135-150.

*Primary Examiner*—Christine Nucker
*Assistant Examiner*—Frederick F. Tsung
*Attorney, Agent, or Firm*—Cushman, Darby & Cushman

[57] ABSTRACT

New echiboline derivatives with opioid properties which are 6-hydroxy-9-methyl-echiboline derivatives having, in the 10-position, a hydrocarbon substituent of up to 4 carbon atoms—preferably a group $R.CH_2$— (wherein R represents a hydrogen atom or a hydrocarbon group of up to 3 carbons) and especially a methyl, cyclopropyl-methyl or allyl group.

These are made by dealkylating corresponding 6-alkoxy-9-methyl-10-substituted echibolines, thereby converting the 6-alkoxy group to a 6-hydroxy group, especially using boron tribromide as dealkylating reagent.

Specific examples are 6-hydroxy-9,10-dimethyl-echiboline, 6-hydroxy-9-methyl-10-allyl-echiboline and 6-hydroxy-9-methyl-10-cyclopropylmethyl-echiboline.

The compounds may be in free base or salt form, and be incorporated as active ingredient into pharmaceutical compositions.

Also, the corresponding 6-alkoxy-9-methyl-10-substituted echiboline derivatives as useful novel intermediates, which may be made from a 6-alkoxy-9-methyl-echiboline by (A) reaction with a reagent which introduces the desired substituent into 10-position or (B) acylating to introduce the substituent R—CO— into the 10-position and reducing the acyl group to $RCH_2$—.

8 Claims, 3 Drawing Sheets

LOG CONCENTRATION (ng/ml)

LOG CONCENTRATION (ng/ml)

NEW ORGANIC COMPOUNDS HAVING OPIOID PROPERTIES

This invention relates to new organic compounds having opioid properties, and to methods for their production.

It is known that eseroline, a hydrolysis product of physostigmine, has analgesic properties approximately equipotent with morphine but it also retains undesirable anticholinesterase activity.

Analogues of eseroline have been described in 1982 by Bartolini et al, in Canadian Patent Specification No. 1,137,489, but without presentation of any supporting pharmacological data.

Well known and potent analgesics include compounds having the molecular skeleton of morphine with addition of a substituted 2-carbon atom bridge between the 6 and 14 carbon atoms in the morphine structure, but this modification of the structure still has not taken away the high dependence liability.

It appears to be very difficult to identify, in any compound which possesses valuable opioid properties akin to those of morphine, exactly what causes the highly undesirable properties of respiratory depression, vomiting and dependence liability commonly associated with morphine.

The varied actions of morphine are mediated via a range of different types of receptors and it is believed that a particular action (for example analgesia) may be mediated via one type of receptor while a different type of receptor mediates another action, for example dependence liability. These different types of opioid receptors exist in peripheral tissues which can therefore serve as "models" for assessing opioid activity. In this way, the action of a drug on the intestinal muscle of the guinea pig, for example, is indicative of analgesic activity in man. The spectrum of sensitivity of different types of receptors (the receptor "profile") in a range of isolated tissues towards various opioids can thus be used as an indication of differences in properties which are of importance in practical use, for example the degree of dependence liability.

The existence of opioid antagonists at these receptors assist in the identification of novel mechanisms of drug action (i.e. receptor "profiles" that differ from morphine).

It is therefore very important to find compounds which do have opioid properties including the desired features but with the less desirable features removed or diminished, i.e. opioid compounds which have a different receptor "profile" from that of morphine itself.

We have now found that the opioid activity of eseroline can be retained to a substantial degree while the anticholinesterase activity appears to be substantially reduced or even removed, by incorporating a bridge structure in the eseroline ring system, namely a four-carbon atom bridge. Additionally, such compounds have opioid receptor "profiles" that differ from that of morphine and so are indicative of different qualitative actions in vivo, and offer an alternative to morphine.

Thus according to our invention we provide new organic compounds having opioid properties, namely new echiboline derivatives which are 6-hydroxy-9-methyl-echibolines with a hydrocarbon substituent of up to 4 carbon atoms in the 10-position.

The compounds of this invention, being bases, form salts with acids. Accordingly, the present invention includes the compounds in the form of the free bases or their salts, and the new compounds may be defined as new echiboline derivatives having, in their free-base form, the structure of a 6-hydroxy-9-methyl-echiboline with a hydrocarbon substituent of up to 4 carbon atoms in the 10-position.

The hydrocarbon substituent at the 10-position may contain up to four carbon atoms, and is preferably of the structure $R.CH_2$- wherein R represents a hydrogen atom or a hydrocarbon group of up to three carbons. When R is a hydrocarbon group, this may be for example a cyclopropyl group or an ethenyl group ($CH_2=CH-$), so that the 10-substituent is correspondingly a cyclopropyl-methyl or an allyl group. When R is a hydrogen atom, the 10-substituent is a methyl group. These compounds are especially useful and convenient to make.

Echiboline is the trivial name which has been given by Fritz and Fisher (Tetrahedron, 1964, 20, pages 1737-1753) to the base 1,2,3,4-tetrahydro-9a,4a-(iminoethano)-9H-carbazole.

The new compounds of this invention may therefore be defined alternatively as 1,2,3,4-tetrahydro-6-hydroxy-9-methyl-9a,4a-(iminoethano)-9H-carbazoles with a hydrocarbon substituent of up to 4 carbon atoms in the 10-position.

In particular, specific compounds we provide are: (A) 6-Hydroxy-9,10-dimethyl-echiboline, (B) 6-Hydroxy-9-methyl-10-allyl-echiboline, and (C) 6-Hydroxy-9-methyl-10-cyclopropylmethyl-echiboline. These may be alternatively named, respectively, as: (A) 1,2,3,4-tetrahydro-6-hydroxy-9,10-dimethyl-9a,4a-(iminoethano)-9H-carbazole, (B) 1,2,3,4-tetrahydro-6-hydroxy-9-methyl-10-allyl-9a,4a-(iminoethano)-9H-carbazole, and (C) 1,2,3,4-tetrahydro-6-hydroxy-9-methyl-10-cyclopropylmethyl-9a,4a-(iminoethano)-9H-carbazole.

According to our invention we also provide a process for making the said new compounds of our invention, i.e. the 10-substituted 6-hydroxy-9-methyl-echiboline derivatives, which comprises dealkylating a 6-alkoxy-9-methyl-echiboline having a hydrocarbon substituent of up to 4 carbon atoms in the 10-position and thereby converting the 6-alkoxy group to a free 6-hydroxy group.

The alkoxy group in the 6-position of the echiboline ring system may be a lower alkoxy group, i.e. one containing an alkyl group of 1 to 4 carbon atoms, but the preferred alkoxy group is methoxy, in which case the method comprises the demethylation of a 6-methoxy-9-methyl-10substituted echiboline, for example 6-methoxy-9,10-dimethyl-echiboline.

Thus according to our invention we also provide new echiboline derivatives, useful as intermediates for making the opioid compounds of our invention, namely 6-alkoxy-9-methyl-echiboline derivatives having in the 10-position a hydrocarbon substituent of the structure $R.CH_2-$ wherein R represents a hydrocarbon group of up to three carbon atoms. The 6-alkoxy group may be an alkoxy group containing an alkyl group of 1 to 4 carbon atoms, and preferably a methoxy group.

The de-alkylation step, in which the alkoxy group (especially a methoxy group) of the 6-alkoxy-9-methyl-10-substituted echiboline is converted to a hydroxy group, thus producing the 6-hydroxy-9-methyl-10-substituted echiboline, may be carried out by use of any de-alkylating agent which does not attack the rest of the molecule. The preferred reagent is a boron halide, for example boron tribromide.

The boron tribromide may be used for this purpose in the manner conventional for O-dealkylation, for example in solution in a non-polar organic solvent (for example a halogenated alkane, most conveniently dichloromethane or mixtures thereof) under hot and anhydrous conditions (conveniently at 60 to 90 degrees C.), followed by hydrolysis by addition of water or by addition of a hydroxy compound, for example an alkanol and conveniently methanol.

According to our invention we also provide a process for making the new intermediate compounds (the 6-alkoxy-9-methyl-10-substituted echibolines) which comprises reacting a 6-alkoxy-9-methyl-echiboline with a reagent which introduces the desired hydrocarbon substituent into the 10-position.

Especially, the process for making the compounds is carried out using a reagent of the structure R—CH$_2$-Halogen, wherein R has the meaning above. Examples of the preferred reagents for this purpose include allyl bromide.

According to our invention we also provide a process for making the 6-alkoxy-9-methyl-10-substituted echibolines which comprises acylating a corresponding 6-alkoxy-9-methyl-echiboline to form the corresponding 6-alkoxy-9-methyl-10-acyl-echiboline and then reducing this 6-alkoxy-9-methyl-10-acyl-echiboline whereby the carbonyl group of the acyl group is converted to a methylene group.

The acylation introduces the substituent R.CO— (wherein R has the meaning stated above) into the 10-position. Acylation may be carried out using conventional techniques and acylating agents, for example the acid halides or anhydrides derived from the carboxylic acid R.COOH.

For example the reaction may be formylation, in which case the product after reduction is the 10-methyl derivative (i.e. a 6-alkoxy-9,10-dimethyl-echiboline). Alternatively, substituents other than methyl can be introduced into the 10-position, as for example by using cyclopropyl carboxylic acid anhydride or chloride to introduce the cyclopropylcarbonyl group (CH$_2$)$_2$CH.CO— into the 10-position and then reducing this to the cyclopropylmethyl group (CH$_2$)$_2$CH.CH$_2$—.

The 6-alkoxy-9-methyl-echiboline may be made by reduction of the corresponding ($\pm$)-9-methyl-6-alkoxy-11-oxo-echiboline, for example ($\pm$)-9-methyl-6-alkoxy-11-oxo-echiboline.

These oxo-compounds, which are cyclic amides, can be made by a modification of the Fischer indole reaction from N-alphamethyl 4-methoxyphenylhydrazine and ethyl cyclohexanone-2-acetate. This method is analogous to the method described by Fritz and Stock [Tetrahedron, 26, 5821–5829, (1970)] for the synthesis of the homologous compound 2-oxo-8-methyl-5-methoxy-2,3-dihydro-1H,8H-3a,8a-propanopyrrolo-[2,3,b]-indole from N-alpha-methyl 4-methoxyphenylhydrazine and ethyl cyclopentanone-2-acetate. The ethyl cyclohexanone-2-acetate can be made by the method described by Segre, Viterbo and Parisi, [J.Am.Chem.Soc., 79, 3503–3505 (1957)]. The N-alphamethyl 4-methoxyphenylhydrazine can be made by the method described by Spath and Brunner [Chem. Ber., 58, 518–523 (1925)].

The ($\pm$)-9-methyl-6-alkoxy-11-oxo-echibolines, for example ($\pm$)-9-methyl-6-alkoxy-11-oxo-echiboline, is then reduced so as to convert the carbonyl group at the 11-position of the echiboline ring to a methylene group. A suitable reagent for this purpose is any which can reduce the carbonyl of an amide to methylene, for example lithium aluminium hydride.

According to our invention we also provide a process for making a 6-alkoxy-9,10-dimethyl-echiboline which comprises reduction of the corresponding 9,10-bis-formyl derivative of a 6-alkoxy-echiboline.

The 9,10-bis-formyl derivative of a 6-alkoxy-echiboline may be made by formylation of the corresponding 6-alkoxy-echiboline. Formylation may be carried out using conventional formylating agents which formylate the imino groups of heterocyclic compounds, but it is preferred to use acetic-formic anhydride (alone or in solution in a solvent, for example acetic acid). The acetic-formic anhydride may be made in pure form by the known reaction between sodium formate and acetyl chloride, or it may be made in impure form (though still effective for the purposes of this invention) by reacting together formic acid and acetic anhydride to produce acetic-formic anhydride in admixture with acetic acid.

The 6-alkoxy-echiboline may be made by the reaction of 4-alkoxy-phenylhydrazine with 2-(2-chloroethyl)-cyclohexanone. This reaction can be carried out at elevated temperature (especially at about 60 to 70 degrees C.) in solution in a polar organic solvent and is a modification of the Fischer indole synthesis. Examples of suitable solvents for this purpose include lower alkanols (by which we mean alkanols having up to four carbon atoms in the molecule) for example methanol, ethanol, and mixtures thereof.

The reduction may be accomplished by any reagent which reduces the carbonyl group of the acyl group to a methylene group (for example reduces a formyl group to a methyl group) without attacking the rest of the molecule. The preferred reducing agent for the purpose is lithium aluminium hydride. This may be used in conventional manner, most conveniently in an inert polar solvent, for example tetrahydrofuran.

These processes are especially convenient for making 6-methoxy-9,10-dimethyl-echiboline.

The new 6-hydroxy-9-methyl-10-substituted echiboline derivatives may be made, stored or used as salts, especially in the form of pharmaceutically acceptable salts, for example the hydrochloride or hydrobromide.

In some cases, it is found that the free bases are unstable or tend to be difficult to purify—possibly through a tendency of the product to oxidise in basic solution. Consequently, it is then preferred to make (and also to store) the products as salts instead of as the free bases. Salts can be made directly, avoiding the necessity to liberate the free base, for example by using boron tribromide as the dealkylating agent convert the 6-alkoxy group to a 6-hydroxy group and allowing the hydrobromide (usually di-hydrobromide) to crystallise directly from the reaction mixture without basifying the reaction medium and solvent-extracting the free base. The resulting salt (for example hydrobromide) may be purified by recrystallisation.

This direct formation of the salt may be achieved simply by adjusting the solvent medium in which the reaction product is prepared so that the salt has a sufficiently low solubility to cause it to come out of solution. In the case of the boron tribromide dealkylation method, the variation can be to add an organic hydroxy compound (preferably an alkanol, and most conveniently methanol) instead of water after dealkylation has taken place. This is especially applicable to the products in which the 10-substituent is unsaturated or cyclic, for example allyl or cyclopropylmethyl.

The compounds of the invention may be used in man or animals for their effects on opioid receptors of the peripheral and central nervous systems. For this purpose they may be used in the form of formulations containing the compound together with conventional adjuvants, diluents and the like as are suitable for enteral and parenteral administration. Accordingly the invention also provides pharmaceutical compositions comprising a compound as active ingredient.

The invention is illustrated but not limited by the following Examples, in which parts and percentages are by weight unless stated otherwise.

PROCEDURES

Melting points were measured on a Kofler hot stage apparatus and are uncorrected. Ultraviolet, infra-red, $^1$H-nmr and mass spectra were recorded on a Perkin-Elmer model 402 spectrophotometer, a Pye Unicam model SP3-100 spectrophotometer, either a Perkin-Elmer model R12B 60-MHz or a Bruker model WP80 80-MHz spectrophotometer (TMS was used as internal standard) and a Kratos model MS-25 instrument connected to a DS-55 data output terminal, respectively. Tlc was formed using Polygram Alox N/UV$_{254}$ plates (0.2 mm) supplied by Camlab, Cambridge. Column chromatography was effected upon Brockmann grade 1 alumina supplied by BDH.

EXAMPLE 1

Preparation of (±)-9,10-Di-Methyl-6-Hydroxy-Echiboline

A solution of boron tribromide (478 mg) in dichloromethane (5 ml) was added, in one portion, to a solution of (±)-9,10-di-methyl-6-methoxy-echiboline (53 mg) in dichloromethane (5 ml) cooled to −78 degrees C. The mixture was allowed to warm slowly to ambient temperature over a period of 2 hours, and then boiled under reflux conditions for 1 hour, and then cooled again to ambient temperature. Then water (3 ml) was added and the mixture was neutralised by addition of sodium carbonate. The organic (dichloro-methane) phase was then separated and dried over anhydrous magnesium sulphate, and the solvent was removed by evaporation. The resulting product was a brown oil (42 mg, 83% yield).

Physical properties measured were:

TLC (Ethanol/Chloroform, 1:9 by volume): R$_f$=0.63, (Compare R$_f$ of the starting material, which is 0.86 under the same conditions), IR (Chloroform): 3280 cm$^{-1}$ (broad) (OH), MS: m/e=258 (100%) (M+), 243 (5.7%) (M+-CH$_3$), 229 (5.9%), 201 (92.5%) [M+-(CH$_2$)$_2$NCH$_3$].

The di-hydrochloride crystallised from a mixture of ethanol and ether as pale tan prisms, melting point 205–207 degrees C. (with sintering from 184–186 degrees C.).

Elemental analysis of the product gave the result:

Found: C 54.2, 54.1, 53.7; H 7.25, 7.4, 7.0; N 7.8, 8.9, 7.1; Cl 22.4.

[C$_{16}$H$_{23}$Cl]$_2$N$_2$O requires C 58.9, H 7.3, N 8.45, Cl 21.4%]

$^1$H-nmr (D$_2$O): δ=7.57 ppm. (1H$_d$) (H$_8$) (J$_{ortho}$=11 Hz); 7.07 ppm. (1H$_d$) (H$_5$) (J$_{meta}$=4 Hz); 7.00 ppm. (1H$_{dd}$)H$_7$ (J$_{ortho}$=11 Hz, J$_{meta}$=4 Hz); 3.90 ppm. (3 Hs) (N$_9$-CH$_3$); 2.42 ppm. (3 Hs) (N$_{10}$-CH$_3$); 3.25–1.37 ppm. (12 Hm) (methylene envelope):

MS: m/e=258 (63.6%) (M+), 243 (3.8%), 229 (4.9%), 201 (100%).

Preparation of intermediates for above:

Preparation of (±)-6-Methoxy-Echiboline

Equimolar proportions of 4-methoxy phenylhydrazine (2.76 g, 0.02 mole) [Frahn and Illman, Australian J. Chem., 1974, 27, 1361–1365] and 2-(2-chloroethyl)-cyclohexanone [Volodina, Kiryushkina and Terent'ev, Dokl. Akad. Nauk. S.S.S.R., 1965 162, (1), 90–93] (3.20 g, 0.02 mole) were dissolved in ethanol (20 ml) and the mixture was heated at boiling temperature under reflux conditions for 8 hours. The ethanol was then removed by evaporation, to leave a red-brown oily residue. This residue was digested with 0.1 molar aqueous hydrochloric acid (200 ml) at approximately 70 degrees C. to dissolve soluble material. The mixture was then cooled to ambient temperature and neutral acid-insoluble materials were removed by extraction with di-ethyl ether.

The aqueous acid layer was then basified by addition of sodium hydroxide, conveniently as solid caustic soda pellets, and the resulting gummy precipitate was extracted with chloroform (twice, using portions of 60 ml each). The chloroform extracts were combined and then dried by addition of anhydrous magnesium sulphate, the chloroform was removed by evaporation, and the residual dark brown oil was purified by column chromatography on a column of neutral alumina, using chloroform as the carrier solvent.

The purified product was obtained as a brown oil which crystallised after standing for several days. It was recrystallised from petroleum ether (boiling range 60–80 degrees C.) to form pale cream coloured crystals, melting point 88–89 degrees C.

Elemental analysis of the product gave the result:

Found: C 74.0; H 8.6; N 11.7%.

[C$_{15}$H$_{20}$N$_2$O requires C 73.75; H 8.25; N 11.45%].

Physical properties measured were:

$^1$H-nmr (CDCl$_3$): δ=6.65 ppm. (3H$_m$)(H,H$_7$,H$_8$); 3.75 ppm. (3Hs) (OCH$_3$); 2.85 ppm. (2H$_b$) (CH$_2$N); 2.40 ppm. (2H$_b$) (D$_2$O exchanged) (2 xNH); 2.10–1.50 ppm. (10H$_{bm}$) (methylene envelope).

MS: m/e=244 (87%)(M+); 201 (97%) (M+-CH$_2$=CH.NH$_2$); 200 (100%) (M+- (CH$_2$)$_2$ NH$_2$).

UV (in MeOH):

λ max 230 nm (log ε=4.02), 280 nm (log ε=3.85); UV (in MeOH/HCl):

εmax 248 nm (log ε=3.89), 320 nm (log ε=3.84).

Preparation of (±)-9,10-Di-Formyl-6-Methoxy-Echiboline (Method A)

A mixture of acetic anhydride (2 ml) and formic acid (1 ml) was heated at 50–70 degrees C. for 2 hours, and then cooled to 0 degrees C. and (±)-6-methoxy-echiboline (25 mg) was added with stirring, under anhydrous conditions. The resulting pale-brown solution was allowed to warm to ambient temperature, then water (50 ml) was added and the mixture was neutralised by addition of solid sodium carbonate and then extracted with chloroform (three times, using 8 ml portions each time). The chloroform extracts were combined and washed with a saturated aqueous solution of sodium carbonate (10 ml), dried with anhydrous sodium carbonate, and then the chloroform was removed by evaporation. The residue was purified by column chromatography on a column of basic alumina, using a mixture (1:1 by volume) of chloroform and petroleum ether (boiling range 60–80 degrees C. as the carrier solvent.

This produced the bis-formyl derivative as a pale brown oil (22 mg, 71% yield).

Preparation of
(±)-9,10-Di-Formyl-6-Methoxy-Echiboline
(Method B)

A solution of acetic-formic anhydride (1 ml) in dichloromethane (2 ml) was added dropwise under anhydrous conditions to a stirred solution of (±)-6-methoxy-echiboline (123 mg) in dichloro-methane (5 ml) at 0 degrees C. with cooling. The mixture was then allowed to warm to ambient temperature and stirring was continued overnight. Then water was added and the di-formyl derivative was isolated in the same way as described in procedure (B.2) above, i.e. by extraction with chloroform. (133 mg., 88% yield).

The properties of the products made by Methods A and B above were identical, namely:

TLC (Chloroform): $R_f=0.26$.

IR (liquid film):
Transparent between 4000 and 3100 cm$^{-1}$ (no NH); 1660 cm$^{-1}$ (C=O).

MS: m/e=300 (4.5%)(M$^+$); 272 (35%) (M$^+$—CO); 200 (40%) (M$^+$—CO—CH$_2$=CHNHCHO).

Preparation of
(±)-9,10-Di-Methyl-6-Methoxy-Echiboline

A solution of (±)-9,10-di-formyl-6-methoxy-echiboline (216 mg) in tetrahydrofuran (25 ml) was boiled under anhydrous reflux with lithium aluminium hydride (0.72 g) for 3 hours. The excess of lithium aluminium hydride was then decomposed by dropwise addition of water and the suspended white solid was removed by filtration and washed well with tetrahydrofuran. The combined filtrate and washings were combined and dried (using anhydrous sodium carbonate) and the tetrahydrofuran solvent was removed by evaporation. The residue from the evaporation was purified by column chromatography on a neutral alumina column, using a mixture (1:1 by volume) of chloroform and petroleum ether (boiling range 60–80 degrees C.) as the carrier solvent, to provide the product as a pale brown oil (118 mg, 60% yield), boiling point 160–165 degrees C. at 0.01 mm Hg.

Physical properties measured were:

TLC (60–80 petroleum ether:chloroform, 1:1): $R_f=0.25$.

IR (liquid film): Transparent between 4000 and 3100 cm$^{-1}$ and between 1800 and 1610 cm$^{-1}$ (no NH or =CO).

MS: m/e=272 (98%) (M$^+$); 257 (9%) (M$^+$- CH$_3$); 215 (100%) (M$^+$-CH$_2$=CH.NH.CH$_3$); 200 (20%) (215-CH$_3$).

$^1$H-nmr (CDCl$_3$); δ=6.60 ppm. (2H$_m$) (H$_5$,H$_7$); 6.15 ppm. (1H$_d$) (H$_8$) (J$_{ortho}$=12 Hz.); 3.70 ppm. (3H$_s$) (OCH$_3$); 2.75 ppm. (5H$_s$) (N$_9$-CH$_3$/N$_{10}$-CH$_2$); 2.40 ppm. (3H$_s$) (N$_{10}$-CH$_3$); 2.00–1.30 ppm. (10H) (multiplet) (methylene envelope), UV (in MeOH): ε max 255 nm (log ε=3.95), 324 nm (log ε=3.44), UV (in MeOH/HCl) λ max 247 nm (log ε=3.81), 319 nm (log ε=3.78).

The base was also characterised as its picrate, which was obtained from ethanol as yellow needles, melting point 149–150 degrees C.

Elemental analysis of the picrate gave the result:

Found: C 54.9; H 5.5; N 13.9%.
[C$_{23}$H$_{27}$N$_5$O$_8$ requires C 55.1; H 5.45; N 13.95%].

The free base was liberated from the picrate by treatment with sodium hydroxide solution, extraction with chloroform, passage of the chloroform solution through a short basic alumina column and removal of the solvent, and had spectral data identical with those given above.

EXAMPLE 2

Preparation of
(±)-9,10-Di-Methyl-6-Hydroxy-Echiboline

A solution of boron tribromide (2 g) in dichloromethane (20 ml) was added, in one portion, to a solution of (±)-9,10-di-methyl-6-methoxy-echiboline (0.2 g) in dichloro-methane (20 ml) cooled to −78 degrees C. The mixture was allowed to warm slowly to ambient temperature over a period of 2 hours and then boiled under reflux for 1 hour and then cooled again to ambient temperature. Then water (12 ml) was added and the mixture was neutralised by addition of sodium carbonate. The organic (dichloro-methane) phase was then separated from the aqueous phase and the aqueous phase was washed with chloroform (twice, using 20 ml portions each time). The organic phases were combined and dried over anhydrous magnesium sulphate and the solvent was removed by evaporation. The resulting product was a pale brown oil (0.182 g, 95.9% yield).

The di-hydrochloride was immediately prepared, crystallised from a mixture of ethanol and di-ethyl ether as pale tan prisms, melting point 207–209 degrees C. (with seating from 185–187 degrees C.).

Physical properties measured were: MS: m/z=258 (23.3%) (M$^+$), 201 (36.0%) (M$^+$-CH$_2$=CH-NH.CH$_3$);

$^1$H-nmr (D$_2$O): δ=7.50 ppm. (1H$_d$) (H$_8$) (J$_{ortho}$=11 Hz); 7.02 ppm. (1H$_s$) (H$_5$); 6.95 ppm. (1H$_d$) (H$_7$) (J$_{ortho}$=11 Hz); 3.89 ppm. (3H$_s$) (N$_9$-CH$_3$); 2.89 ppm. (3H$_s$) (N$_{10}$-CH$_3$); 3.3–1.0 ppm. (12H$_m$) (methylene envelope).

Preparation of intermediates for above:

Preparation of
(±)-9-Methyl-6-Methoxy-11-Oxo-Echiboline

A solution of 4-methoxy-N-alpha-methyl phenylhydrazine (6.95 g) with ethyl cyclohexanone-2-acetate (8.79 g) [Segre, Viterbo and Parisi, et al., J.Am.Chem.-Soc., 79, 3503–3505 (1957)] in benzene (sodium dried; 40 ml), with 3 drops of glacial acetic acid added, was boiled under reflux conditions employing a Dean & Stark separator until no further water was separated (two hours). The benzene was then removed by evaporation leaving a red-brown oily residue to which glacial acetic acid (25 ml) was added. The mixture was boiled under reflux for 1.5 hours. The acetic acid was the removed by evaporation, to leave a brown oily residue. This residue was dissolved in chloroform (500 ml). The chloroform solution was shaken with aqueous hydrochloric acid (6M) four times, using 200 ml portions each time. The hydrochloric acid extracts were combined and ice (200 g) added followed by strong ammonia solution (0.88) to achieve basification. The resultant solid was removed by filtration (3.8 g, 30.6% yield).

The material recrystallised from methanol as pale cream plates melting point 227–229 degrees C.

Physical properties measured were: IR (KCl disc): 1685 cm$^{-1}$ (C=O).

MS: m/z=272 (100%) (M$^+$), 257 (26.5%) (M$^+$-CH$_3$).

$^1$H-nmr (CDCl$_3$): δ=6.75 ppm. (1H$_d$) (H$_7$) (J$_{ortho}$=12 Hz); 6.65 ppm. (1H$_s$) (H$_5$); 6.40 ppm. (1H$_d$) (H$_8$) (J$_{ortho}$=12 Hz); 3.75 ppm. (3H$_s$) (OCH$_3$); 2.70 ppm. (3H$_s$) (N$_9$ —CH$_3$); 2.60 ppm. (2H$_s$) (N$_{10}$—CO—CH$_2$); 2.10–1.20 ppm. (8H$_{6M}$) (methylene envelope).

Elemental analysis of the product gave the result:
Found: C 70.3; H 7.6; N 9.9%.
[C$_{16}$H$_{20}$N$_2$O$_2$ requires C 70.7; H 7.4; N 10.3%].

Preparation of (±)-6-Methoxy-9-Methyl-Echiboline

A solution of (±)-9-methyl-6-methoxy-11-oxo-echiboline (2.81 g) in tetrahydrofuran (500 ml) was added with stirring to a suspension of lithium aluminium hydride (1.51 g) in tetrahydrofuran (100 ml). The mixture was boiled under anhydrous reflux for 16 hours. The excess of lithium aluminium hydride was then decomposed by dropwise addition of a saturated aqueous solution of sodium sulphate and the suspended white solid was removed by filtration and washed with di-ethyl ether. The organic phase was separated and the aqueous phase shaken with di-ethyl ether (three times, using 100 ml portions each time). The organic phases were combined and dried (using anhydrous magnesium sulphate) and the solvent was removed by evaporation. The resulting product was a brown oil, (2.12 g, 74.4% yield).

Physical properties measured were:
IR (liquid film): 3300 cm$^{-1}$ (broad) (N-H), Transparent between 1800 and 1610 cm$^{-1}$ (no =CO);
MS: m/z=258 (56.7%) (M$^+$); 243 (12.4%) (M$^+$-CH$_3$); 228 (16.2%) (243 - CH$_3$); 215 (27.8%) (M$^+$-CH$_2$=CH.NH$_2$).

$^1$H-nmr (CDCl$_3$); δ=6.60 ppm. (2H$_m$) (H$_5$ and H$_7$); 6.20 ppm. (1H$_d$) (H$_8$) (J$_{ortho}$=12 Hz); 3.75 ppm. (3H$_s$) (OCH$_3$); 2.81 ppm. (2H$_s$) (N$_{10}$-CH$_2$); 2.65 ppm. (3H$_s$) (N$_9$ - CH$_3$); 2.1–1.2 ppm. (11H$_{6m}$) (methylene envelope and N-H (D$_2$O exchanged).

The base was also characterised as its picrate which was obtained from ethanol as yellow-orange needles, melting point 170–172 degrees C.

Elemental analysis of the picrate gave the result:
Found: C 54.6; H 5.4; N 14.6%.
[C$_{22}$H$_{25}$N$_5$O$_8$ requires C 54.2; H 5.2; N 14.4%].

The free base was liberated from the picrate by treatment with sodium hydroxide solution, extraction into chloroform, passage of the chloroform solution through a short basic alumina column and removal of the solvent, and had spectral data identical with those given above.

Preparation of
(±)-9-Methyl-10-Formyl-6-Methoxy-Echiboline

A solution of acetic-formic anhydride (6 ml) in dichloromethane (10 ml) was added dropwise under anhydrous conditions to a stirred solution of (±)-9-methyl-6-methoxy-echiboline (0.613 g) in dichloro-methane (20 ml) at 0 degrees C. with cooling. The mixture was then allowed to warm to ambient temperature and stirring was continued overnight. Then water (50 ml) was added and the mixture was neutralised by addition of solid sodium carbonate and then extracted with chloroform (three times, using 20 ml portions each time). The chloroform extracts were combined and washed with a saturated aqueous solution of sodium carbonate (50 ml), dried with anhydrous sodium carbonate and the organic solvent was removed by evaporation, to give a brown oil (0.662 g, 91.5% yield).

Physical properties measured were:
IR (liquid film): Transparent between 4000 and 3100 cm$^{-1}$ (no NH); 1660 cm$^{-1}$ (no =CO);
MS: m/z=286 (100%) (M$^+$); 271 (20.4%) (M$^+$-CH$_3$); 215 (41.0%) (M$^+$-CH$_2$=CH.NH.CHO);

$^1$H-nmr (CDCl$_3$); δ=8.4 ppm. (1H$_s$) (—CHO); 6.65 ppm. (2H$_m$) (H$_5$ and H$_7$); 6.30 ppm. (1H$_d$) (H$_8$) (J$_{ortho}$=12 Hz); 3.74 ppm. (3H$_s$) (OCH$_3$); 2.70 ppm. (3H$_s$) (N$_9$ - CH$_3$); 2.30–1.10 ppm. (12H$_m$) (methylene envelope).

Preparation of
(±)-9,10-Di-Methy3-6-Methoxy-Echiboline

A solution of (±)-9-methyl-10-formyl-6-methoxy-echiboline (0.60 g, 0.002 mole) in tetrahydrofuran (50 ml) was heated at boiling temperature under anhydrous reflux conditions with lithium aluminium hydride (0.70 g, 0.019 mole) for 3 hours. The excess of lithium aluminium hydride was then decomposed by dropwise addition of a saturated aqueous solution of sodium sulphate, and the suspended white solid was removed by filtration and washed well with di-ethyl ether. The organic phase was separated and the aqueous phase shaken with di-ethyl ether (three times, using 100 ml portions each time). The organic phases were combined and dried (using anhydrous magnesium sulphate) and the sol vent was removed by evaporation, to give a brown oil, (0.36 g, 62.1% yield).

Physical properties measured were:
IR (liquid film):
Transparent between 4000 and 3100 cm$^{-1}$, and between 1800 and 1610 cm$^{-1}$ (no NH or =CO);
MS: m/z=272 (70.2%) (M$^+$); 257 (8.3%) (M$^+$-CH$_3$); 215 (84.3%) (M$^+$-CH$_2$=CH.NH.CH$_3$); 200 (18.3%) (215 - CH$_3$).

$^1$H-nmr (CDCl$_3$); δ=6.60 ppm. (2H$_m$) (H$_5$, H$_7$); 6.20 ppm. (1H$_d$) (H$_8$) (J$_{ortho}$=12 Hz); 3.74 ppm. (3H$_s$) (OCH$_3$); 2.76 ppm. (5H$_s$) (N$_{10}$-CH$_3$, N$_{10}$-CH$_2$); 2.43 ppm. (3H$_s$) (N$_9$-CH$_3$); 2.30–1.25 ppm. (10H$_m$) (methylene envelope).

The base was further characterised as its picrate, which was obtained from ethanol as yellow needles, melting point 151–155 degrees C. (Literature value 149–150 degrees C.).

EXAMPLE 3

Preparation of
(±)-9-Methyl-10-Cyclopropylmethyl-6-Hydroxy-Echiboline

A solution of boron tribromide (0.658 g) in dichloromethane (2.6 ml) was added dropwise, over a period of 30 minutes, to a stirred solution of (±)-9-methyl-10-cyclopropylmethyl-6-methoxy-echiboline (0.2 g) in dichloromethane (4.6 ml) cooled to 1 degree C. The mixture was allowed to warm to ambient temperature over a period of 2 hours and then it was partially concentrated by solvent evaporation. The mixture was then chilled to 0 degrees C. using an ice bath, and methanol (1.5 ml) was added dropwise. After stirring the cooled solution for 15 minutes ethyl acetate was added to afford a pale yellow crystalline material (0.213 g, 72.2% yield) of the desired compound as its dihydrobromide salt, melting point 193–195 degrees C. The compound was recrystallised from a mixture of methanol and ethyl acetate.

Physical properties measured were:
MS: m/z =29B (12.8%) (M$^+$), 243 (2.6%) 214 (6.2%) 201 (52.4%)

¹H-nmr (D₂O): δ=7.60 ppm. (1H$_d$) (H$_8$) (J$_{ortho}$=11 Hz); 7.13 ppm. (1H$_d$) (H$_5$) (J$_{meta}$=4 Hz); 7.03 ppm. (1H$_{dd}$) (H$_7$) (J$_{ortho}$=11 Hz, J$_{meta}$=4 Hz); 3.9 ppm. (3Hs) (N$_9$-CH$_3$); 3.2-1.3 ppm.(14H$_m$) (N$_{10}$-CH$_2$, N$_{10}$-CH$_2$, (methylene envelope);
1.0-0.15 ppm. (5H$_m$) (cyclopropyl).
Elemental analysis of the product gave the result:
Found: C 47.6; H 6.3; N 5.6; Br 34.7%.
[C$_{19}$H$_{28}$N$_2$OBr$_2$ requires C 49.6; H 6.1; N 6.1; Br 34.7%]
Preparation of intermediates for above Preparation of
(±)-9-Methyl-10-Cyclopropylcarboxy-6-Methoxy-Echiboline A solution of cyclopropyl-carboxylic acid anhydride (8 ml) in dichloro-methane (20 ml) was added dropwise under anhydrous conditions to a stirred solution of (±)-9-methyl-6-methoxy-echiboline (0.8 g) in dichloro-methane (40 ml) at 0 degrees C. with cooling. The mixture was then allowed to warm to ambient temperature and stirring was continued overnight. Then chloroform (60 ml) was added and the mixture was shaken with 3M aqueous hydrochloric acid (four times, using 50 ml portions each time). Ice (100 g) was added to the combined aqueous extracts and the solution was basified with strong aqueous ammonia solution (0.88). This mixture was shaken with chloroform (four times, using 50 ml portions each time). The chloroform extracts were combined, dried with anhydrous sodium carbonate and then the organic sol vent was removed by evaporation to give a brown oil (0.886 g, 87.7% yield). The material crystallised on standing.
Physical properties measured were:
IR (liquid film): Transparent between 4000 and 3100 cm$^1$ (no N-H); 1630 cm$^{-1}$ (C=O).
MS: m/z=326 (72.0%) (M$^+$); 311 (3.2%) (M$^+$-CH$_3$); 215 (56.6%) (M$^+$-CH$_2$=CH—NH.CO.cyclopropyl); ¹H-nmr (D$_2$O): δ=6.70 ppm. (2H$_m$) (H$_5$ and H$_7$); 6.30 ppm. (1H$_d$) (H$_8$) (J$_{ortho}$=12 Hz); 3.76 ppm. (3H$_s$) (CH$_3$O); 2.93 ppm. (3Hs) (N$_9$-CH$_3$); 2.2-3.0 ppm. (3H$_m$) (N$_{10}$—CH$_2$, CO—CH); 1.7-1.4 ppm. (10Hm) (methylene envelope); 0.98-0.6 ppm. (4H$_m$) (cyclopropyl dimethylene).
Elemental analysis of the product gave the result:
Found: C 73.7; H 8.2; N 8.55%.
[C$_{20}$H$_{26}$N$_2$O$_2$ requires C 73.6; H 8.0; N 8.58%].

Preparation of
(±)-9-Methyl-10-Cyclopropylmethyl-6-Methoxy-Echiboline

A solution of (±)-9-methyl-10-cyclopropylcarboxy-6-methoxy-echiboline (0.886 g) in tetrahydrofuran (100 ml) was boiled under reflux with lithium aluminium hydride (0.62 g) for 4 hours. The excess of lithium aluminium hydride was then decomposed by dropwise addition of a saturated aqueous solution of sodium sulphate and the suspended white solid was removed by filtration and washed with di-ethyl ether. The organic phase was separated and the aqueous phase washed well with di-ethyl ether (three times, using 50 ml portions each time) The organic phases were combined and dried (using anhydrous magnesium sulphate) and the solvent removed by evaporation, to give a brown oil, (0.79 g, 93.2% yield). The material was crystallised from diethyl ether by cooling the solution in a Dewar flask containing solid carbon dioxide and had melting point 33-34 degrees C.

Physical properties measured were: IR (KCl disc)
Transparent between 4000 and 3100 cm$^{-1}$ and between 1800 and 1610 cm$^{-1}$ (no NH or =CO);
MS: m/z=312 (34.2%) (M$^+$); 297 (2.0%) (M$^+$-CH$_3$); 215 (94.2%) (M$^+$-CH$_2$=CH.NH.CH$_2$.cyclopropyl); 200 (13.6%) (215 - CH$_3$);
¹H-nmr (CDCl$_3$);
δ=6.60 ppm. (2H$_m$) (H$_5$ and H$_7$); 6.15 ppm. (1H$_d$) (H$_8$) (J$_{ortho}$=12 Hz); 3.74 ppm. (3H$_s$) (OCH$_3$); 2.67 ppm. (3H$_s$) (N$_9$-CH$_3$); 3.5-2.2 ppm. (4H$_m$) (N$_{10}$-CH$_2$, N$_{10}$-CH$_2$); 2.0-1.2 ppm. (10H$_m$) (methylene envelope); 1.0-0.3 ppm.(5H$_m$) (cyclopropyl).
Elemental analysis of the product gave the result:
Found: C 76.7; H 9.2; N 8.9%.
[C$_{20}$H$_{28}$N$_2$O requires C 76.9; H 9.0; N 8.95%].
The base was also characterised as its picrate which was obtained from ethanol as yellow-orange needles, melting point 111-113 degrees C.
Elemental analysis of the picrate gave the result:
Found: C 57.8; H 5.8; N 12.7%.
[C$_{26}$H$_{31}$N$_2$O requires C 57.7; H 5.8; N 12.9%].
The free base was liberated from the picrate by treatment with sodium hydroxide solution, extraction with chloroform, passage of the chloroform solution through a short basic alumina column and removal of the solvent and had spectral data identical with those given above.

EXAMPLE 4

Preparation of
(±)-9-Methyl-10-Allyl-6-Hydroxy-Echiboline

A solution of boron tribromide (0.329 gl in dichloro-methane (2.5 ml) was dropwise, over a period of 30 minutes, to a stirred solution of (±)-9-methyl-10-allyl-6-methoxy-echiboline (0.093 g) in dichloro-methane (5 ml) cooled to 1 degree C. The mixture was allowed to warm to ambient temperature over a period of 2 hours and then it was partially concentrated by solvent evaporation. The mixture was then chilled using an ice bath (to 0 degrees C.) and methanol (1 ml) was added dropwise. After stirring the cooled solution for 15 minutes, ethyl acetate was added to afford a pale yellow crystalline material (0.073 g, 52.5% yield) of the desired compound as its di-hydrobromide salt, melting point 184-186 degrees C. The compound was recrystallised from a mixture of methanol and ethyl acetate.
physical properties measured were:
MS: m/z=284 (18.0%) (M$^+$), 214 (11.0%) 201 (30.0%)
¹H-nmr (D$_2$O) δ=7.65 ppm. (1H$_d$) (H$_8$) (J$_{ortho}$=11 Hz); 7.13 ppm. (1H$_d$) (H$_5$) (J$_{meta}$=4 Hz); 7.05 ppm. (1H$_d$) (H$_7$ (J$_{ortho}$=11 Hz, J$_{meta}$=4 Hz); 5.7-5.2 ppm. (3H$_m$) (ethene protons); 3.94 ppm. (3H$_s$) (N$_9$-CH$_3$); 3.47 ppm.(2H$_d$) (N—CH$_2$—CH=CH$_2$) (J=7 Hz); 3.25-1.2 ppm. (12H$_m$) (methylene envelope);
Elemental analysis of the product gave the result:
Found: C 45.5; H 6.05; N 6.2; Br 35.2%.
[C$_{18}$H$_{26}$N$_2$OBr$_2$ requires C 48.45; H 5.9; N 6.3; Br 35.8%]
Preparation of intermediates for above:

Preparation of
(±)-9-Methyl-10-Allyl-6-Methoxy-Echiboline

A solution of allyl bromide (freshly distilled) (0.094 g) in dichloro-methane (1.25 ml) and dimethyl formamide (0.5 ml) was added, over a period of 2 hours, with stirring, to a solution of (±)-9-methyl-6-methoxy-echiboline (0.2 g) in dimethyl formamide (5 ml) and water (0.2 ml) to which anhydrous potassium carbonate (0.107 g) had been added. The mixture was then stirred at ambient temperature overnight and then water (50 ml) was added. The mixture was then shaken with dichloromethane (four times, using portions of 30 ml each time). The combined dichloro-methane extracts were then washed with water (four times, using portions of 30 ml each time) and saturated brine (four times, using portions of 30 ml each time), dried (using anhydrous magnesium sulphate), and the solvent was evaporated to give a brown oil (0.118 g, 51.6% yield).

Physical properties measured were: IR (liquid film:
Transparent between 4000 and 3100 cm$^{-1}$ (no NH).
MS: m/z=298 (56.9%) (M+); 283 (3.3%) (M+- $CH_3$); 215 (100%) (M+-$CH_2$=CH.NH—$CH_2$.CH=$CH_2$); 200 (21.0%) (215-$CH_3$).

$^1$H-nmr ($CDCl_3$); δ=6.60 ppm. ($2H_m$) ($H_5$ and $H_7$); 6.20 ppm. ($1H_s$) ($H_8$) ($J_{ortho}$=12 Hz); 5.25–4.96 ppm. ($3H_m$) (ethene protons); 3.73 ppm. ($3H_s$) ($OCH_3$); 2.70 ppm. ($3H_s$) ($N_9$-$CH_3$); 3.6–2.3 ppm. ($4H_m$) ($N_{10}$-$CH_2$, $N_{10}$-$CH_2$); 2.06–1.0 ppm. ($10H_m$) (methylene envelope).

Biological Testing: Procedures and Results

The actions of 6-hydroxy-9,10-dimethyl-echiboline alternatively named 1,2,3,4-tetrahydro-6-hydroxy-9,10-dimethyl-9a,4a-(iminoethano)-9H-carbazole) on the opioid receptors of the guinea pig ileum and mouse vas deferens were compared with those of its chemical analogue eseroline and its pharmacological analogue morphine.

Additional tests have also been made for analgesic and anti-cholinesterase activities.

The actions of the two other echiboline derivatives—6-hydroxy-9-methyl-10-allyl-echibolineand6-hydroxy-9-methyl-opropylmethyl-10-cyclopropyl-methyl-echiboline—on peripheral opioid receptors are also summarized.

Transmurally stimulated guinea pig ileum

Sections of guinea-pig ileum were set up for transmural stimulation under a resting tension of 0.75 g in Krebs solution bubbled with 5% carbon dioxide in oxygen at 37 degrees C according to the method of Kosterlitz and Watt (1968) Contractions were elicited from stainless steel electrodes, one of which was sited in the lumen at supramaximal voltage and a frequency of 0.05 Hz. Isometric contractions were recorded on a Rikadenki recorder. Potential agonists were added directly to the bath and the contact time was until maximum inhibition had occurred. The responses of the preparation in the presence of naloxone were examined with the naloxone present in the physiological solution. Results were expressed as percent inhibition. In each experiment a log dose effect relationship was determined using at least four concentrations in the absence of antagonist, and then in the presence of one or more concentrations of naloxone.

Mouse vas deferens preparation

Vasa deferentia were removed and mounted in 1.2 ml tissue baths under a resting tension of 200 mg in $Mg^{2+}$-free Krebs solution bubbled with a mixture of 95% oxygen and 5% carbon dioxide at 36 degrees C. The preparations were left for 1 hour to equilibrate. Contractions were elicited from platinum electrodes fused to the sides of the tissue bath using supramaximal voltage (usually above 100 V), a pulse width of 1ms and a frequency of 0.1 Hz. Isometric contractions were recorded on a Grass polygraph. As with the ileum, concentration effect relationships were determined in the absence then presence of naloxone.

Compounds used for comparison of their effects were morphine sulphate, naloxone hydrochloride, eseroline and (±)-6-hydroxy-9,10-dimethyl-echiboline hydrochloride. Eseroline was dissolved in minimal 0.1N hydrophloric acid and dilutions made with water. Salts were dissolved in water.

Analgesic tests

Analgesic activity was assessed using two methods in mice—the Hot Plate Test and the Abdominal Constriction Test (acetic acid). The test drug was given by subcutaneous injection and the results expressed as $ED_{50}$ with 95% confidence intervals.

Anticholinesterase Test

Anticholinesterase activity was assessed using the method of Ellman, Courtney et al., (1961) using guinea pig ileum as the enzyme source.

Guinea-pig ileum

In concentrations up to 200 ng/ml, eseroline caused a concentration-dependent inhibition of contractions induced by transmural stimulation. This represented a maximum inhibition of about 50%. Increasing the concentration caused no further inhibition. This inhibitory action was antagonised by naloxone in a concentration-dependent manner (0.5, 5 and 50 ng/ml). In concentrations above 400 ng/ml, and in the presence of naloxone, eseroline enhanced electrically-induced contractions of the muscle. This is illustrated in FIG. 1.

Figure 2:
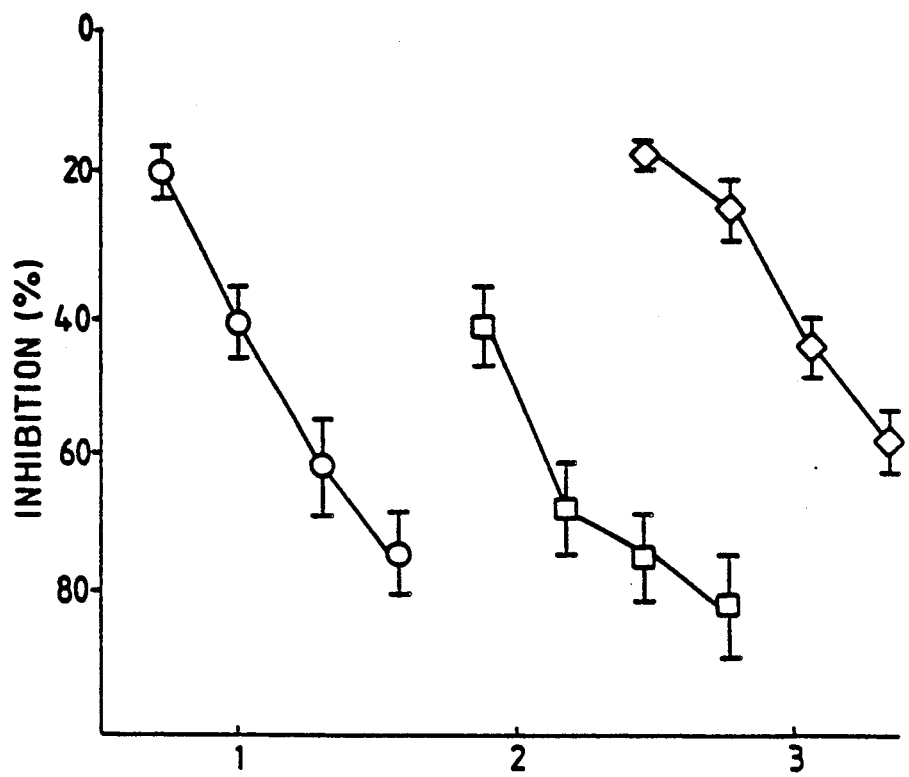
Figure 2:
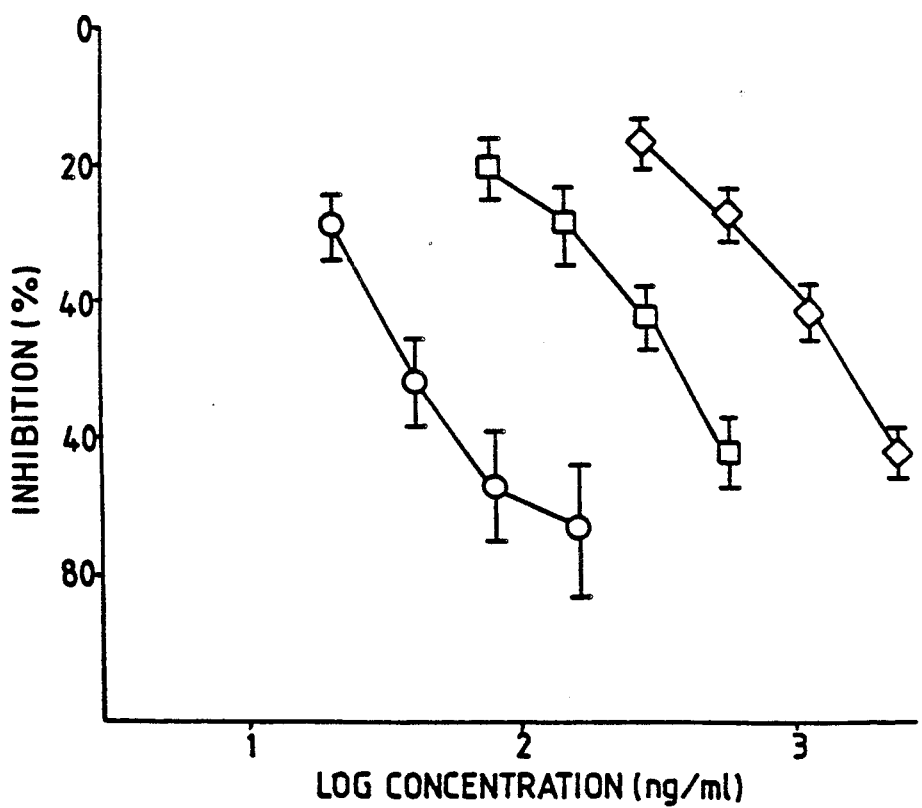

Log concentration-effect curves for morphine alone and in the presence 5 and 50 ng/ml naloxone are included in FIG. 2. Morphine caused the familiar inhibition of the preparation and naloxone antagonism was confirmed.

(±)-6-hydroxy-9,10-dimethyl-echiboline similarly inhibited the electrically-induced contractions of the guinea pig ileum. It too was antagonised by naloxone in a concentration-dependent manner.

In contrast to eseroline, at no stage was an excitatory stage seen, and the maximum degree of inhibition of the preparation exceeded 50%, with some individual values showing over 90% inhibition.

The potencies of morphine and (±)-6-hydroxy-9,10-dimethyl-echiboline represented by their $EC_{50}$ values are compared in Table 1. The $EC_{50}$ values are calculated from bulked controls. Morphine was found to be 2.8 times more potent than (±)-6-hydroxy-9,10-dimethyl-echiboline on this preparation.

6-Hydroxy-9-methyl-10-allyl-echiboline inhibited contractions of the ileum with an $IC_{50}$ of 0.3 ug/ml, it being about ten times less potent than morphine. It was antagonized by naloxone (5 and 50 ng/ml), and the characteristics of antagonism clearly indicated interaction with a different receptor population than that with which morphine interacts.

In concentrations up to 50 ng/ml 6-hydroxy-9-methyl-10-allyl-echiboline had no antagonist activity against morphine in this preparation.

6-Hydroxy-9-methyl-10-cyclopropylmethyl-echiboline also inhibited the contractions of the ileum, but was of weaker potency with an $IC_{50}$ in excess of 1ug/ml. Naloxone had little antagonist activity. The cyclo derivative had no detectable antagonist activity against morphine in this preparation.

Mouse vas deferens

Figure 3:
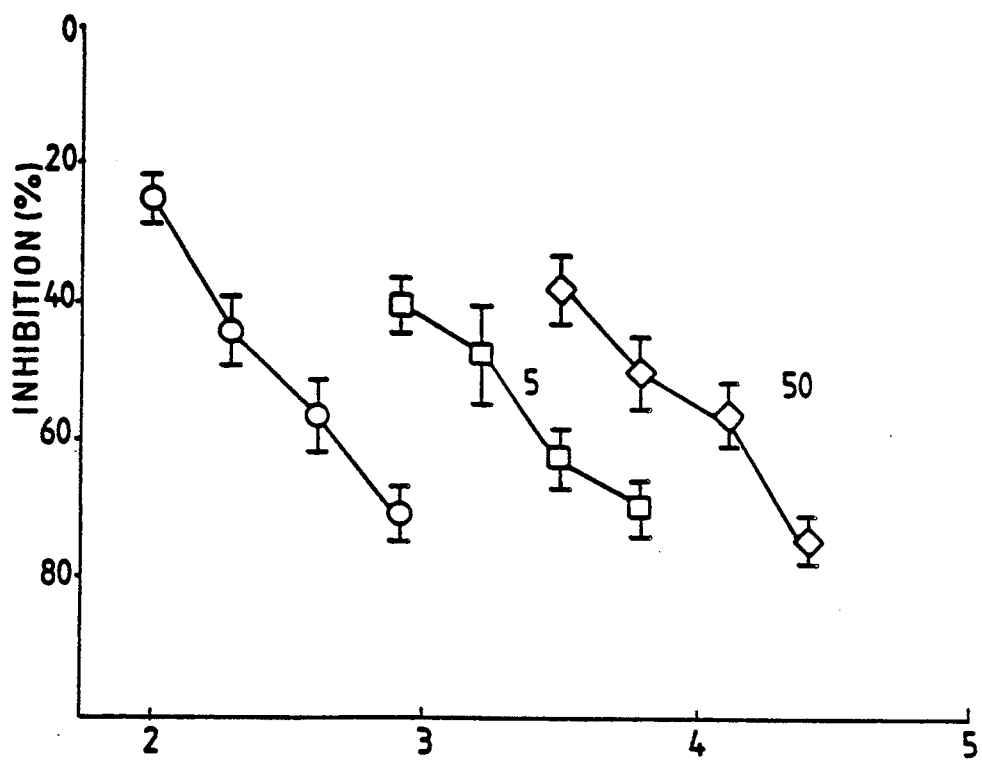
Figure 3:
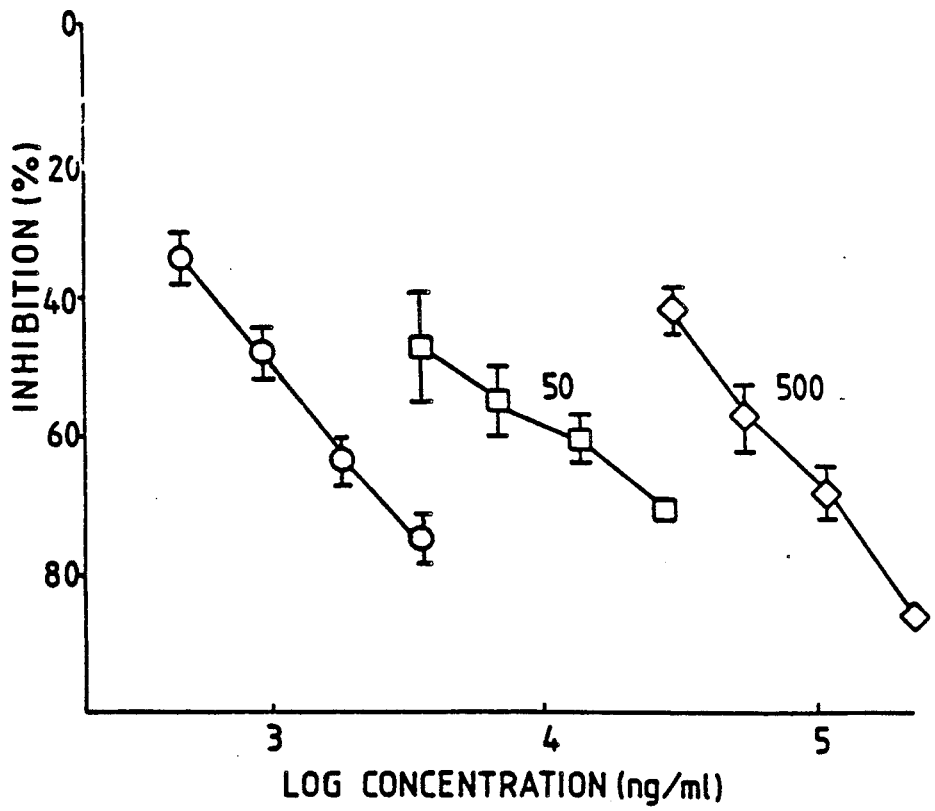

Concentration-effect lines for morphine and (±)-6-hydroxy-9,10-dimethyl-echiboline alone and in the presence of naloxone are shown in FIG. 3. $EC_{50}$ values for the two compounds are compared in Table 2, from which it can be seen that morphine was 3.6 times more potent than (±)-6-hydroxy-9,10-dimethyl-echiboline on this preparation.

Table 2 gives an estimate of the degree of antagonism by naloxone of the two opioid derivatives expressed as the log dose ratios of the shifts in concentration-effect lines. The values are derived from individual comparisons of the percentage inhibition of the preparations in the presence of a concentration of naloxone and that in the same preparation in the absence of naloxone.

Whilst naloxone is clearly an antagonist of (±)-6-hydroxy-9,10-dimethyl-echiboline it is some ten times less effective as an antagonist than against morphine since the antagonism of morphine by 5 and 50 ng/ml naloxone quantitatively matches the antagonism of (±)-6-hydroxy-9,10-dimethyl-echiboline by 50 and 500 ng/ml.

In contrast to eseroline, 6-hydroxy-9,10-dimethyl-echiboline showed no evidence of cholinesterase inhibitory activity which otherwise characterises "cholinomimetic" analgesic compounds.

When the potencies of morphine and 6-hydroxy-9,10-dimethyl-echiboline were compared on the two preparations in the absence then presence of the opioid antagonist naloxone, the results indicate that the receptor selectivity of 6-hydroxy-9,10-dimethyl-echiboline differs from that of morphine, and also this novel opioid structure differs clearly from other opioid "type" substances. This is indicative of a different spectrum of activity in vivo.

These results confirm that eseroline has opiate activity and evidence for anti-cholinesterase activity was also seen. The enhancement of transmural contractions of the ileum at high concentrations is characteristic of a cholinesterase inhibitor and is compatible with published data for anticholinesterase activity of eseroline. The action of (±)-6-hydroxy-9,10-dimethyl-echiboline on the ileum showed no evidence of cholinesterase inhibition. No enhancement of contractions was seen, and progressive opiate-like inhibition of the preparation progressed to close to 100%.

The guinea-pig ileum and the mouse vas deferens contain different populations of the different types of opiate receptors and differences between potency ratios of agonists on the two preparations have often been used to distinguish between different receptor selectivities (for example Paterson et al., Br. Med. Bull., 39 (1983), pages 31-36). Additionally, naloxone is a more potent antagonist of opiate agonists at some types of receptors than others, and thus naloxone susceptibility has also been used to provide evidence of receptor interactions.

These results also show that (±)-6-hydroxy-9,10-dimethyl-echiboline possessed opiate-like activity on two well-documented "models" of central activity and, on the above basis, that the receptor population which mediates the effects of (±)-6-hydroxy-9,10-dimethyl-echiboline differs from that of morphine.

Analgesic activity predicted from the in vitro screen was confirmed using two standard animal tests. Naloxone was an effective antagonist, and the behaviour of the mice was suggestive of "morphine-like" activity.

Substitution of the N-methyl substituent of an opioid compound with a bulky substituent (for example allyl) causes a change in pharmacological activity which may be a. a change from an agonist to an antagonist, b. a change in the receptor selectivity of the agonist, c. a change to a drug which posseses both agonist and antagonist activities.

6-Hydroxy-9-methyl-10-allyl-echiboline possesses opioid agonist activity in vitro which is suggestive of analgesic activity in vivo. The relative lack of potency of naloxone as an antagonist is compatible with this agonist activity being mediated via a receptor different from that with which morphine acts. This receptor is likely to be the "kappa" receptor. Agonists at the kappa receptor commonly have low dependence liability.

Analgesic Testing in Mice $ED_{50}$ and 95% confidence intervals.
mg/kg, subcutaneous injection.

| | 6-hydroxy-9,10-dimethyl echiboline | morphine |
| --- | --- | --- |
| Hot Plate | 1.71 (1.34–2.18) | 3.22 (2.88–3.62) |
| Abdominal Constriction (Acetic acid) | 0.23 (0.15–0.38) | 0.41 (0.28–0.63) |

The drug was antagonised by naloxone. The potency relative to morphine is somewhat greater than that predicted from the in vitro tests.

Anticholinesterase Test

Using guinea pig ileum as enzyme source, the echiboline derivative had no detectable anti-cholinesterase inhibitory activity in concentrations up to 6.4 ug/ml.

TABLE 1

| | $EC_{50}$ (±SD) | |
| --- | --- | --- |
| | Guinea-pig ileum (ng/ml) | Mouse vas deferens (g/ml) |
| Compound A | 12.1 (7.4–19.9) | 0.283 (0.143–0.559) |
| Compound B | 33.5 (23.8–47.1) | 1.014 (0.728–1.413) |

Results show mean of not less than 12 determinations with S.D. range.

TABLE 2

| | Naloxone (ng/ml) | | |
| --- | --- | --- | --- |
| | 5 | 10 | 500 |
| Compound A | | | |
| Ileum | 0.85 (+0.11) | 1.91 (+0.10) | |
| Vas deferens | 0.53 (+0.16) | 1.50 (+0.23) | |
| Compound B | | | |
| Ileum | 0.91 (+0.27) | 1.54 (+0.22) | |
| Vas deferens | | 0.87 (+0.19) | 1.66 (+0.13) |

The shifts in the log dose response curves on guinea-pig ileum and mouse vas deferens caused by naloxone, expressed as log dose ratios (±S.D.). The results show mean of not less than 6 determinations.

Compound A is morphine.

Compound B is (±)-6-hydroxy-9,10-dimethyl-echiboline.

KEY TO DETAILS SUMMARISED IN FIGS. 1 TO 3

FIG. 1

The effects of eseroline on electrically induced contractions of guinea pig ileum
 alone,
 ☐ in the presence of naloxone (0.5 ng/ml),
 in the presence of naloxone (5 ng/ml),
 Δ in the presence of naloxone (50 ng/ml).
Mean±s.e.m. of between 6 and 20 determinations.

FIG. 2

The effects of morphine (A) and (±)-6-hydroxy-9,10-dimethyl-echiboline (B) on electrically induced contractions of the guinea pig ileum
 alone,
 ☐ in the presence of naloxone (5 ng/ml),
 in the presence of naloxone (50 ng/ml).
Mean±s.e.m. of between 6 and 12 determinations.

FIG. 3

The effects of morphine (A) and (±)-6-hydroxy-9,10-dimethyl-echiboline (B) on electrically induced contractions of the mouse vas deferens alone and in the presence of naloxone. The concentrations of naloxone were:
In Panel (A):
 ☐ 5 ng/ml and
 50 ng/nJ,
In Panel (B):
 ☐ 50 ng/ml and
 500 ng/nl.
Mean±s.e.m. of between 6 and 12 determinations.

We claim:

1. Echiboline derivatives, useful as opiates, having the structure of a 6-hydroxy-9-methyl-echiboline with a hydrocarbon substituent of up to 4 carbon atoms in the 10-position, and salts thereof.

2. Echiboline derivatives as claimed in claim 1, wherein the hydrocarbon substituent in the 10-position is of the structure $R.CH_2-$ wherein R represents a hydrogen atom or a hydrocarbon group of up to three carbons.

3. Echiboline derivatives as claimed in claim 2 wherein R is a cyclopropyl or ethenyl ($CH_2=CH-$), so that the 10-substituent is correspondingly a cyclopropyl-methyl or an allyl group.

4. 6-Hydroxy-9,10-dimethyl-echiboline.

5. 6-Hydroxy-9-methyl-10-allyl-echiboline.

6. 6-Hydroxy-9-methyl-10-cyclopropylmethyl-echiboline.

7. Pharmaceutical compositions comprising a compound as claimed in any one of claims 1 to 6 as active ingredient.

8. Use as an opioid of a compound as claimed in any one of claims 1 to 6 or a composition as claimed in claim 7.

* * * * *